United States Patent [19]

Lander

[11] Patent Number: 5,116,483
[45] Date of Patent: May 26, 1992

[54] COMB FOR AFFINITY CO-ELECTROPHORESIS

[75] Inventor: Arthur D. Lander, Brookline, Mass.

[73] Assignee: Massachusetts Institute of Technology, Cambridge, Mass.

[21] Appl. No.: 587,536

[22] Filed: Sep. 21, 1990

Related U.S. Application Data

[62] Division of Ser. No. 432,570, Nov. 6, 1989, abandoned.

[51] Int. Cl.⁵ .............. B01D 61/42; C25B 1/00
[52] U.S. Cl. .............. 204/299 R; 204/182.8
[58] Field of Search ............ 204/299 R, 182.8

[56] References Cited

U.S. PATENT DOCUMENTS

| | | | |
|---|---|---|---|
| 2,147,458 | 2/1939 | Rohland | 204/299 R |
| 3,485,445 | 2/1970 | Williamson | 73/61.1 |
| 3,616,387 | 10/1971 | Siebert et al. | 204/299 R |
| 3,888,759 | 6/1975 | Elson et al. | 204/299 R |
| 4,061,561 | 12/1977 | Fletcher et al. | 204/299 R |
| 4,136,007 | 1/1979 | Fujimori | 204/299 R |
| 4,199,428 | 4/1980 | Hayashi et al. | 204/299 R |
| 4,234,400 | 11/1980 | Kaplan | 204/299 R |
| 4,294,684 | 10/1981 | Serwer | 204/299 R |
| 4,588,491 | 5/1986 | Kreisher et al. | 204/299 R |
| 4,693,804 | 9/1987 | Serwer | 204/182.1 |
| 4,909,918 | 3/1990 | Bambeck et al. | 204/299 R |

OTHER PUBLICATIONS

BIO-RAD: Chromatography, Electrophoresis, Immunochemistry, Molecular Biology, and HPLC price list P, 3/90 (exerpt).
1990 GIBCO BRL Catalog Reference Guide (exerpt).

*Primary Examiner*—T. Tung
*Assistant Examiner*—Caroline Koestner
*Attorney, Agent, or Firm*—Edward R. Gates

[57] ABSTRACT

The invention provides methods and devices for conducting affinity electrophoresis and for characterizing, identifying, selecting, separating and/or isolating molecules based upon affinity. Acceptor molecules are dispersed in discrete lanes within a gel and test molecules are electrophoresed simultaneously through the lanes. Therapeutics may be screened, heterogeneous mixes may be separated and affinity equilibrium constants determined. Special combs and casting trays for forming gels also are provided, as well as the gels formed thereby. An electrophoresis box also is provided.

7 Claims, 6 Drawing Sheets

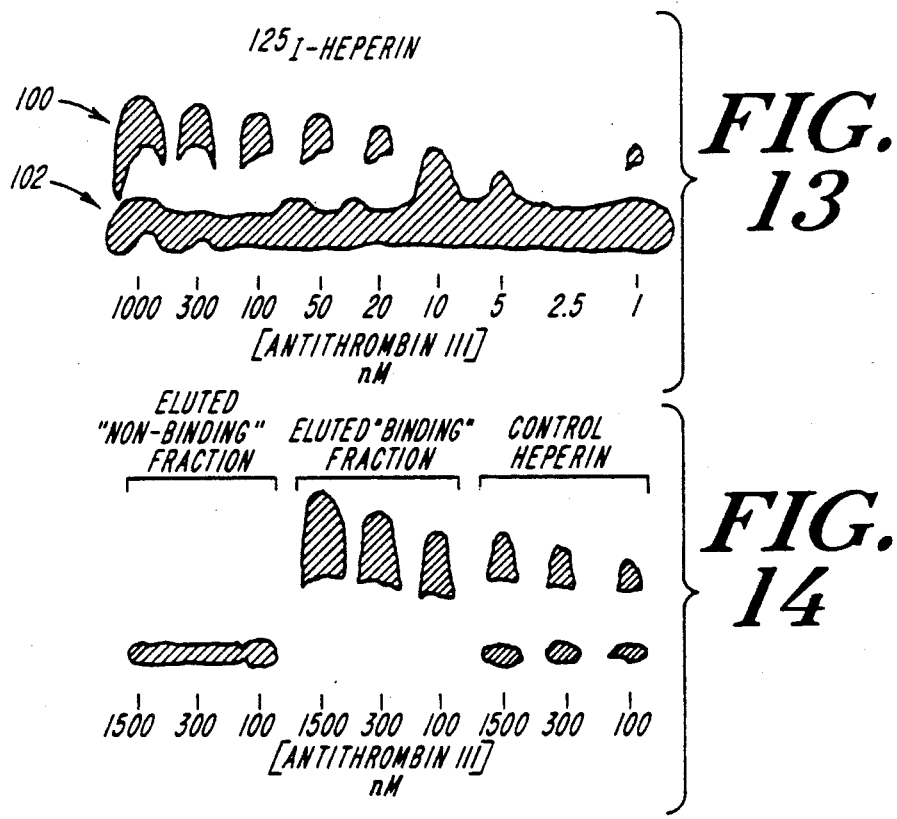
FIG. 13
FIG. 14
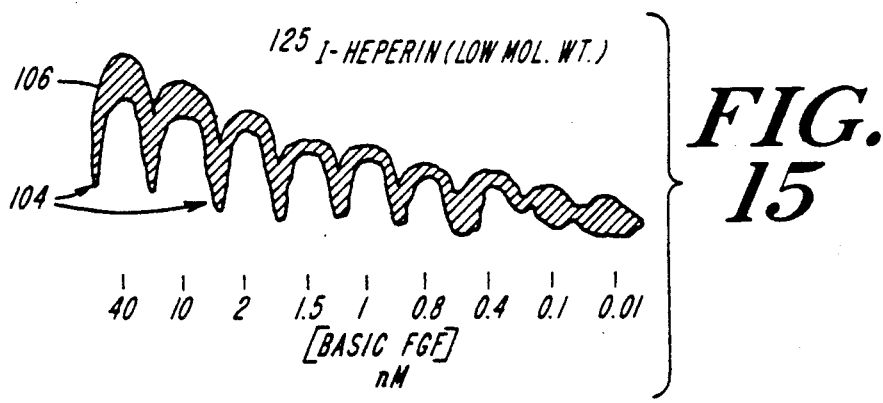
FIG. 15
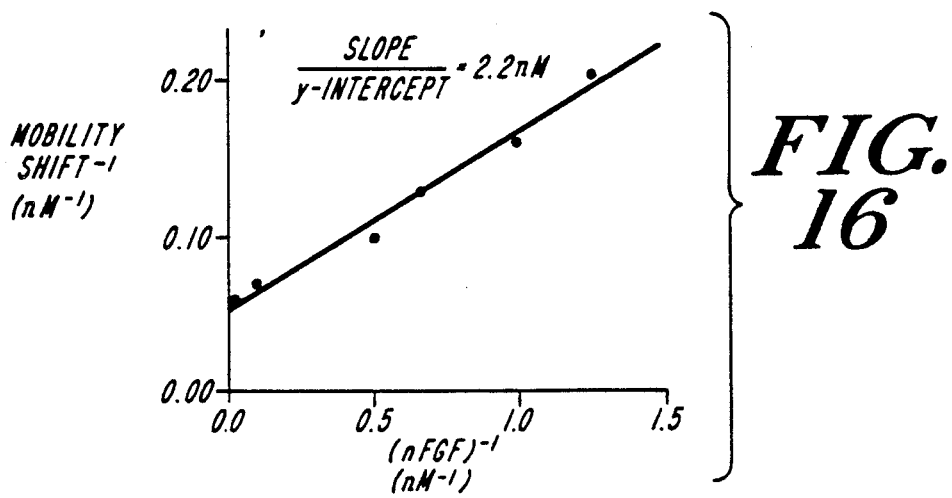
FIG. 16

COMB FOR AFFINITY CO-ELECTROPHORESIS

The Government has rights in this invention pursuant to grant No. BNS 8810400 awarded by the National Science Foundation.

This application is a division of application Ser. No. 07/432,570, filed Nov. 6, 1989, now abandoned.

This invention relates to methods and devices for characterizing, selecting, separating, and/or isolating molecules by affinity electrophoresis.

BACKGROUND OF THE INVENTION

Biological interactions at the molecular level are controlled in part by how tightly various molecules bind one another. Binding between molecules may be used to characterize, select, separate and/or isolate molecules. The present techniques for characterizing, selecting, separating and/or isolating molecules based upon binding, however, are not ideal for use in connection with many molecules.

One measure of the binding between molecules is "affinity". Affinity may be described as the tightness of binding between two molecules at equilibrium. Another measure of binding is the "on-rate", which describes the relative rate at which two unbound molecules tend to form a complex. "Off-rate" describes the relative rate at which a complex of two molecules tends to dissociate.

Affinity separations typically have been carried out using a column with the target molecule ("acceptor") covalently coupled to a solid phase within the column. The test molecule ("ligand") then may be poured over and gravity fed through the column. Ligands having a high affinity for the bound acceptors and low off-rates then will bind to the column with all other molecules passing through the column. The bound ligand molecules then may be eluted from the column using an elution buffer.

This procedure, while acceptable for ligands with high affinities and low off-rates, has many drawbacks. Large amounts of acceptors are required to prepare the column. The acceptor also must be covalently attached to the solid support which typically involves harsh conditions potentially affecting the structure of the acceptor and the affinity between the acceptor and ligand. Moreover, not all acceptors are easily susceptible to covalent linkage to an appropriate solid phase. The procedure also cannot be used when affinity is low and/or off-rate is high. Furthermore, although the procedure can be useful to determine whether two molecules bind tightly, it does not readily yield information on how tight the binding is, or it reveals that information in a manner that cannot be used to determine the "affinity constant" (the affinity constant being the generally accepted numerical representation of "tightness" of binding at equilibrium).

One procedure not requiring covalent linkage of the acceptor to the solid phase of a column has been described. This procedure involves fractionating the ligand on two gravity-fed, gel-filtration columns In one column no acceptor molecules are present. In the other column, acceptor molecules are present throughout the column and in all the liquid that will be passed through the column. The rate at which the ligand moves down each column is a measure of its size. Consequently, if the ligand binds the acceptor in the second column it will move at a rate appropriate for a molecule of larger size.

The procedure has many drawbacks. Large amounts of acceptor are required. The procedure also lacks the sensitivity to detect small changes in molecular size, because nonuniform flow through the column limits resolution. The procedure further depends on preparing two identical columns or on running the same column twice under exactly identical conditions, which can be very difficult An affinity electrophoresis technique involving antibodies or antigens coupled to a gel has been described. According to this procedure, antibodies or antigens are dispersed throughout and covalently linked to the solid phase of a gel. The test molecules then are electrophoresed through the gel containing the immobilized molecules. This procedure has among its drawbacks the problems created by covalent coupling to a solid phase.

SUMMARY OF THE INVENTION

The invention provides methods and devices for conducting affinity electrophoresis. Molecules may be characterized, identified, selected, separated and/or isolated based upon affinity. The invention has particular applications in connection with biologically relevant interactions such as glycosaminoglycan protein complexes, nucleic acid-protein complexes, nucleic acid-nucleic acid complexes, enzyme-substrate interactions, and the interactions of drugs, metabolites, ions, neurotransmitters, cofactors or peptides with proteins. Many of such biologically relevant interactions typically involve cellular ligands and extra-cellular matrix molecules including but not limited to molecules involved in cell attachment, adhesion, growth and inhibitors of the foregoing.

The following represents only a few examples of the numerous utilities of the invention. The invention may be used to screen natural or synthetic molecules and to select those having a potential biological or therapeutic effect based on their affinity for a biological target. The invention also may be used to separate and/or isolate from a heterogeneous mix those molecules having a relatively stronger affinity for a target molecule. Oligonucleotides may be screened to identify those having an affinity for a particular protein. Peptides may be screened to identify those involved in various biological interactions. For example, the identity of peptides which bind to HLA molecules may be determined. The targets of a biologically active molecule such as heparin may be identified. The affinity constant also may be determined according to the novel methods and devices of the invention.

The invention is capable of affinity measurements and separations with very small samples and with high sensitivity. The invention allows affinity measurements and separations to be conducted more quickly than heretofore has been possible. The invention is particularly useful for making measurements or separations of molecules having low affinity and high off-rates, and in particular off-rates ranging from minutes to nanoseconds. The invention also avoids the harsh conditions characteristic of prior art affinity separation techniques.

According to one aspect of the invention, a method for conducting affinity electrophoresis is provided. A gel is prepared containing a dispersion of molecules (acceptors). The acceptor molecules do not need to be linked, covalently or otherwise, to the solid phase of the gel. Test molecules (ligands) are applied to the gel in electrophoretic alignment with the acceptors, the ligands being positioned within the gel at a location remote from the end of the gel towards which the ligands will migrate under the electrophoretic charge. The ligands and acceptors are selected to have relative charges and are positioned with respect to one another so that the ligands will contact the acceptors after an electrophoretic charge is applied. Preferably, the gel is nonrestrictive so that the size of a ligand or acceptor does not significantly hinder its migration compared to what it would be in free solution. The electrophoretic charge is applied for a time period sufficient to permit the migration of the ligands through at least a portion of the gel containing the acceptors. The effect of the acceptors on the migration of the ligands then may be determined, and the gel may be used analytically or preparatively.

Preferably, the acceptors are contained in a plurality of discrete lanes, each lane containing a different concentration of acceptor. Most preferably, the lanes containing acceptors are separated by lanes free of acceptors. Data may be derived from the migration of ligand in the multiple lanes and the affinity constant may be determined.

The foregoing method also may be used for example to separate a heterogeneous mix of ligands. In this instance, if the heterogeneous molecules have substantially the same electrophoretic mobility (such as in a mix of heparin molecules or a mix of oligonucleotides), then the mix of ligands is applied to the gel and electrophoresed through a lane or lanes within the gel containing the acceptor. As the ligands are moved through the gel by electrophoresis, those having an affinity for the acceptor will move more slowly due to their becoming temporarily bound to acceptors. Subfractions thus are separated within the gel according to affinity differences, and the subfractions may be collected from the gel and isolated.

If the mix includes molecules of differing electrophoretic mobility (such as a mix of peptides) then the mix may be first separated within an acceptor-free gel based upon electrophoretic mobility, and then the separated mix may be electrophoresed in gel containing acceptors.

According to another aspect of the invention, a comb adapted for use in preparing a gel for affinity electrophoresis is provided. The comb is capable of forming within a gel a plurality of aligned, parallel troughs, each having a length substantially greater than its width, the troughs being substantially parallel along their lengths. The comb has teeth attached to one another, each tooth having a length, a width, and a height. The length is substantially greater than the width and defines a longitudinal axis. The teeth are oriented with their longitudinal axes being substantially parallel. Preferably, the teeth are rectangular bars having substantially flat, rectangular bottom surfaces lying in the same plane, the teeth being attached to one another remote from their bottom surfaces. The comb also is provided with a gripping handle.

In one embodiment, the comb also includes a rectangular wall spaced from and oriented perpendicular to the longitudinal axes of the teeth and having a length spanning the combined width of the teeth. This wall will form in a gel a single ligand trough spanning the width of the parallel troughs. In yet another embodiment, the comb is provided with a second set of teeth attached to but spaced from the first set of teeth, one each of the second set of teeth aligned with one or more of the first set of teeth. This second set of teeth will form in a gel a plurality of ligand troughs aligned with one or more parallel troughs.

The invention also provides an affinity electrophoresis gel having acceptor molecules dispersed within but not necessarily linked to the solid phase of the gel, the acceptor molecules being confined to at least two separate lanes containing acceptor molecules at different concentrations.

In another aspect of the invention, a casting tray for a gel is provided. The casting tray has attached to it teeth or partitions for forming lanes within a gel. The tray has a bottom and two parallel side walls defining a gel-forming area. Attached to the tray and moveable with respect to the gel-forming area are a plurality of longitudinally aligned and parallel partitions defining between one another parallel channels within the gel-forming area. Preferably, the partitions may be pivoted out of the gel-forming area independent of one another such that the size of the channels defined between the partitions may be adjusted. The tray also may have attached to it a moveable wall for defining within a gel a ligand channel, this wall substantially spanning the combined width of the first channels and substantially perpendicular with respect to the first channels.

According to yet another aspect of the invention, a novel electrophoresis apparatus is provided. The electrophoresis apparatus includes a container having an anode located adjacent to a first side wall and a cathode located adjacent to an opposite, second side wall. A platform is located between the anode and cathode for supporting a gel. The apparatus also includes a chamber associated with the container for receiving a coolant to control the temperature of the gel during electrophoresis and further includes a recirculation loop for recirculating a buffer between the anode and cathode sides of the container to prevent the build up of ions at either end and to control the pH conditions during electrophoresis.

BRIEF DESCRIPTION OF THE DRAWINGS

FIG. 13 is an autoradiogram of an electrophoresed gel containing radioactive ligand according to Example 1;

FIG. 14 is an autoradiogram of an electrophoresed gel containing radioactive ligand according to Example 2;

FIG. 15 is a an autoradiogram of an electrophoresed gel containing radioactive ligand according to Example 3; and FIG. 16 is a graph plotting the movement of the ligand of FIG. 15 with respect to concentration for determining affinity at equilibrium.

DETAILED DESCRIPTION

Figure 1:
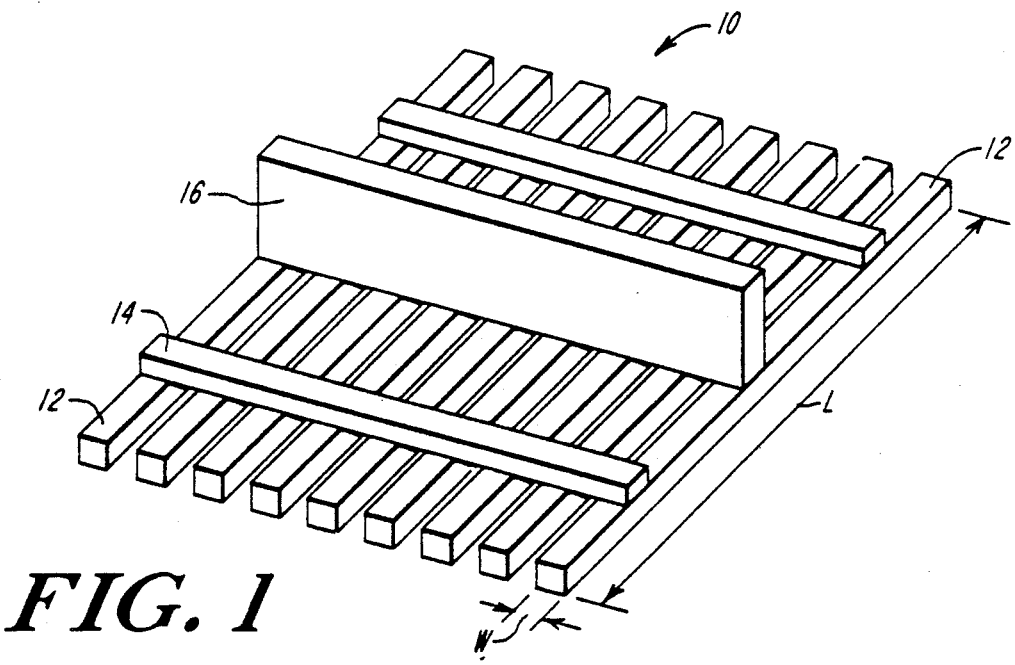
FIG. 1 is a perspective view of a comb of the invention.

The invention involves the characterization, selection, separation and/or isolation of a ligand(s) based upon its affinity for an acceptor. The invention makes use of electrophoresis, which involves placing an electric charge directionally across an electrophoretic medium to cause charged molecules within that medium to migrate. The electrophoretic medium, preferably a gel, may contain acceptors dispersed throughout but preferably unlinked to the solid phase of the gel. The gel preferably is non-restrictive so that ligands move through the gel at a rate reflecting only their mobilities in free solution. Since both the ligand and acceptor in the preferred embodiments may be free to migrate through the gel when an electric field is applied across the gel, it is necessary to apply the acceptor and ligand to the gel in a manner sufficient to permit the ligand to move within the gel and contact the acceptor dispersed throughout the gel. This can be achieved whenever the acceptor and ligand do not have identical electrophoretic mobilities at the operating pH of the electrophoretic system.

According to certain embodiments and particularly those involving affinity determinations, the acceptor is confined within a lane running longitudinally within the gel, and preferably within more than one lane and at a different concentration within each lane. A ligand then is placed in electrophoretic alignment with the lanes. If the acceptor and ligand are nonlinked to the solid phase of the gel, then the relative electrophoretic mobilities of acceptor and ligand determine the appropriate positioning of ligand with respect to acceptor-containing lanes If the acceptor migrates in a direction opposite to that of the ligand, migrates not at all, or migrates in the same direction as the ligand but more slowly than the ligand, then the ligand may be positioned on the side of the acceptor-containing lanes furthest from the pole towards which the ligand is attracted. Thus, the acceptor containing lane is between the ligand and the pole toward which the ligand migrates. In future references, this will be referred to as "standard orientation". If the acceptor migrates in the same direction as the ligand and more rapidly than the ligand, then the ligand must be positioned on the side of the acceptor-containing lanes closest to the pole towards which the ligand is attracted. Thus, in this instance, the ligand will be positioned between the acceptor containing lanes and the pole toward which the ligand migrates. This will be referred to as "inverted orientation". The appropriate choice of orientation ensures that ligand and acceptor molecules come into contact with each other during electrophoresis.

In addition, the invention also is useful even if the ligand and acceptor have the same electrophoretic mobility, so long as the mobility of one with respect to the other may be reduced in the gel. This could be accomplished, for example, by using a gel which interacts with one but not the other, a gel which is physically restrictive to one but not the other, or a gel to which one of the ligand or acceptor is attached, covalently or otherwise.

The relative electrophoretic mobilities of the acceptor and ligand also influence the optimal conditions for electrophoresis in other ways. If the acceptor and ligand move in the same direction, then longer lanes, gels and times for electrophoresis are required to ensure sufficient contact of acceptor and ligands. For optimal resolution, and particularly when determining the equilibrium constant, electrophoresis should be conducted long enough so that ligands in a lane containing no acceptors would migrate to the same position as acceptor molecules that had begun their migration at the end of the acceptor lane farthest from the initial position of the ligands. Empirically, this information usually is easy to obtain by using simple stains (e.g., coomassie blue) to locate acceptors after electrophoresis. Determining how far acceptors will migrate under specific conditions may be determined in control studies performed before or during test runs.

If the acceptors do not move in the electric field, then both the length of the lane(s) containing the acceptors and the time for running the electrophoresis may be shortened. If the acceptors move in a direction opposite to that of the ligands, then the length of the lane(s) containing the acceptors and the time for running the electrophoresis both may be shortened even further while still allowing optimal resolution.

As ligands move through the lanes containing acceptors, ligands and acceptors contact one another and bind reversibly. If the migration rates of the ligands and the acceptors are selected to differ from one another, the migration rate of the acceptor-ligand complexes will be different from that of the ligand. Preferably the acceptor is relatively larger than the ligand. This will enhance the affect on ligand migration caused by ligand-acceptor building.

If on and off rates are slow compared to the duration of the electrophoresis, then aspects of the resulting migration of the ligand may make it difficult or even inappropriate to determine the equilibrium affinity constant. An investigator may determine whether on and off rates are prohibitively slow by carrying out duplicate runs at a number of different voltages. If on and off rates are sufficiently fast for determining the equilibrium affinity constant, then the positions and shapes of the resulting bands across runs should be essentially the same. For many biologically relevant interactions, the off-rates are very fast (minutes to sub-milliseconds) and electrophoresis my proceed quickly (under two hours). Molecules falling into this category of off-rates are ideal for use in the processes of the invention. Biologically relevant complexes with such off-rates include glycosaminoglycan-protein complexes, nucleic acid-protein complexes, many enzyme-substrate interactions and interactions of drugs, metabolites, ions, neurotransmitters, cofactors or peptides with proteins.

Another factor to be considered in determining the conditions of electrophoresis is concentration. If the concentration of the acceptor is very low relative to that of the ligand, then the acceptors will have little effect on the migration of the ligands through the lane containing the acceptors. If the concentration of acceptors is too high, then although preparative techniques still may be carried out, affinity measurements may not be possible. There is a range wherein changes in the concentration of acceptor will result in changes in ligand mobility. For affinity measurements, the acceptor concentration preferably should span the threshold acceptor concentration at which ligand migration is no longer affected and the threshold acceptor concentration at which ligand migration is maximally affected. Since the correct concentrations for making affinity measurements will not always be known by an investigator, the invention advantageously employs multiple, parallel lanes containing different concentrations of acceptors dispersed throughout the gel within the lanes. Moreover, as described in greater detail below, multiple lanes can be used in determining the equilibrium affinity constant for the ligand-acceptor interaction.

The concentration of ligand also will affect migration. If the concentration of the ligand is too high relative to that of the acceptor, most of the ligands will pass unhindered through the dispersion of acceptors. If the concentration of ligand is small compared to the value of the equilibrium affinity constant, then migration of ligand should not be sensitive to the exact concentration of ligand. Thus, for determining the affinity constant, it is not necessary to know the exact ligand concentration, but only to know that the ligand concentration is less than about one-tenth of the value of the equilibrium affinity constant. Control experiments may therefore be performed, wherein different dilutions of ligands are run. An acceptable ligand concentration for experiments intended to measure an affinity constant can be recognized as one for which further dilution of ligand has essentially no effect on the ligand's migration through any of the acceptor-containing lanes.

A preferred procedure for carrying out the processes of the invention will be described in connection with FIGS. 1-4.

To cast the gel of the invention, a casting comb of special design was employed. Referring to FIG. 1, the comb 10 has a plurality of teeth 12. Each tooth is a rectangular bar, the length (L) of each tooth being substantially greater than the width (W) of each tooth. Each tooth defines along its length a longitudinal axis, and the teeth are arranged side by side with their longitudinal axes substantially parallel. Each tooth has a flat, rectangular bottom surface, all of the bottom surfaces lying in the same plane. The teeth are attached to one another remote from their bottom surface by attachment bars 14 which secure the teeth in their planar, parallel array. A handle 16 extends upwardly from the teeth on the same side as the attachment bars remote from the flat bottom surfaces for gripping the comb.

The preferred comb of the invention has nine teeth, each having a length of 1.2 inches, a width of 0.157 inches, and a height of 0.157 inches. The rectangular bars are spaced from one another by 0.118 inches. Preferably, the rectangular bars are made of a non-stick material such as teflon.

To prepare the gel of the invention, an agarose-coated polyester support film 20 is placed on the bottom 22 of a conventional casting tray 18, with the agarose-coated side facing upwardly. The agarose support film 20 is sized in the preferred embodiment to cover the entire surface of the bottom 22 of the casting tray 18. Preferably, the agarose support film 20 is GelBond TM, available from FMC Corporation, Marine Colloids Division, of Rockland, Me.

The open sides of the casting tray 18 are sealed with tape 24 to form a liquid-tight, gel-forming chamber 26 within the casting tray and above the agarose support film 20. A rectangular comb 28 for forming a ligand well then is placed within the chamber 26. The rectangular comb 28 may be formed of a substantially rectangular, thin strip of teflon having the same width as the casting tray 18. The rectangular comb 28 is oriented upright within the chamber 26 spanning the width of the chamber and is held in position by contacting its ends with the tape 24. A line may be drawn on or under the bottom 22 of the casting tray 18 to facilitate proper positioning of the rectangular comb 28. The rectangular comb 28 is notched at either end, the notches 29 providing a channel for the agarose to flow through when the gel is cast so that the ligand trough formed by the rectangular comb 28 does not extend all the way to the sides of the cast gel.

The eletrophoretic medium or framing gel then was prepared for introduction into the casting tray 18. One gram of low-gelling temperature agarose was mixed with 100 ml of electrophoresis buffer and 0.5 grams of detergent, and the mixture was heated to boiling to dissolve the agarose. Low-gelling temperature agarose is well known to those of ordinary skill in the art and is commercially available from a variety of sources. The particular agarose used was Seaplaque TM obtained from FMC. The electrophoresis buffer was either: (a) 0.1M NaCl containing 50 mM PIPES (1), 4-PIPERA-ZINEDIETHANESULFONIC acid) and pH'd to 6.8; or (b) 0.125M sodium acetate containing 50 mM MOPSO(3-]N-MORPHOLINO]PROPANESULFONIC acid) and pH'd to 7.0. Equally good results were obtained with both buffer systems. The detergent used was CHAPS (3-[(3-Cholamidopropyl)-Dimethyammonio]-1-propanesulfonate.) The detergent was used to facilitate the solubility of proteins being analyzed. (When this is not a problem, it is not required.)

The framing gel also may include electrically neutral substances commonly used to stabilize or preserve the solubility of macromolecules [e.g. 2-Mercaptoethanol]. Likewise other substances not electrically neutral, but capable of serving the same purpose, may be included so long as they also are included in the electrophoresis buffer.

Figure 2:
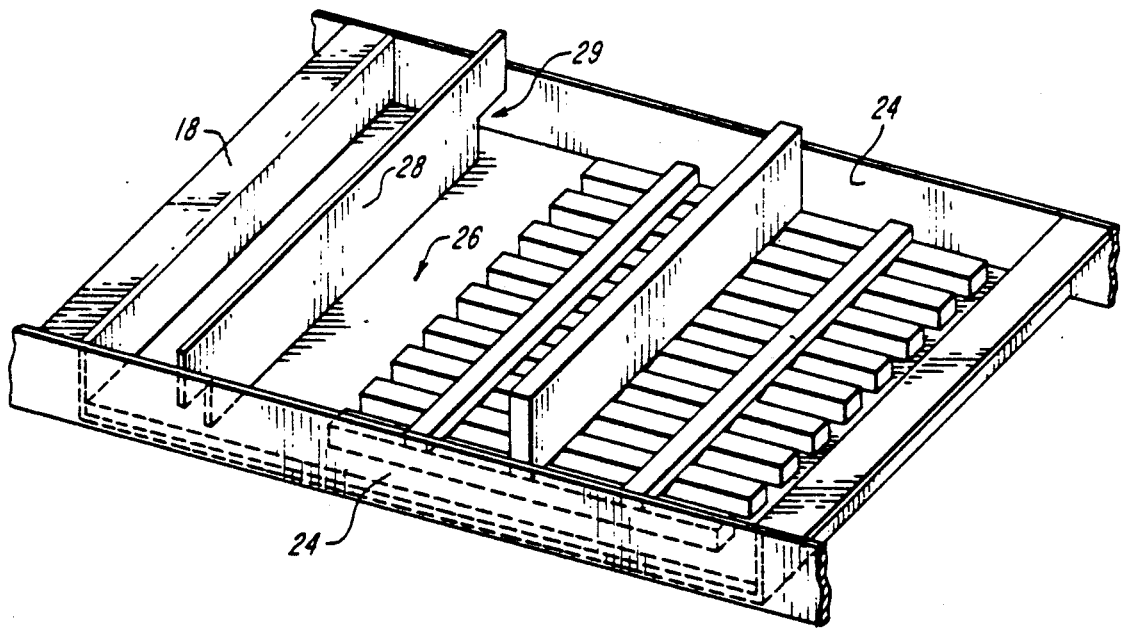
FIG. 2 is a perspective view of the comb of FIG. 1 placed in a casting tray.
Figure 3:
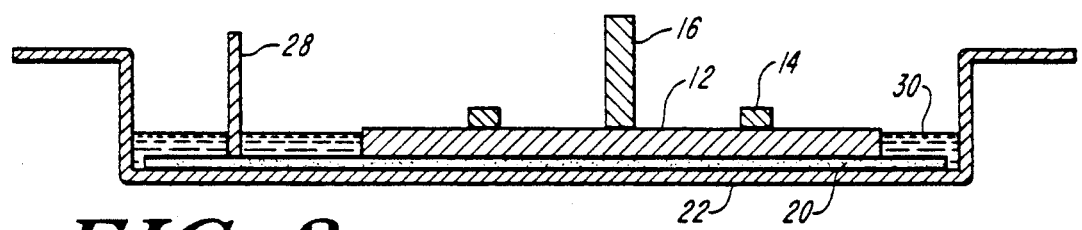
FIG. 3 is a cross-section of the comb and casting tray of FIG. 2, but after gel has been added.

After boiling, the framing gel solution was cooled to between 65 and 80 degrees centigrade, and between 16 and 19 ml of the framing gel 30 was poured into the chamber 26. The comb 10 for forming the parallel lanes then was placed into the framing gel 30 within the chamber 26, the nine rectangular teeth oriented with their lengths parallel to the taped sides of the chamber 26, positioned with their leading edges about two millimeters from the rectangular comb 28 and centered with respect to the rectangular comb 28 (FIG. 2 and FIG. 3). The framing gel 30 then is left undisturbed within the chamber 26 at room temperature until the framing gel 30 fully solidifies. After solidifying, the combs 10 and 28 may be removed. Careful rocking of the combs 10 and 28 will help ease them out of the solidified gel without tearing the gel. Chilling the solidified gel also will strengthen it against possible stresses.

Figure 4:
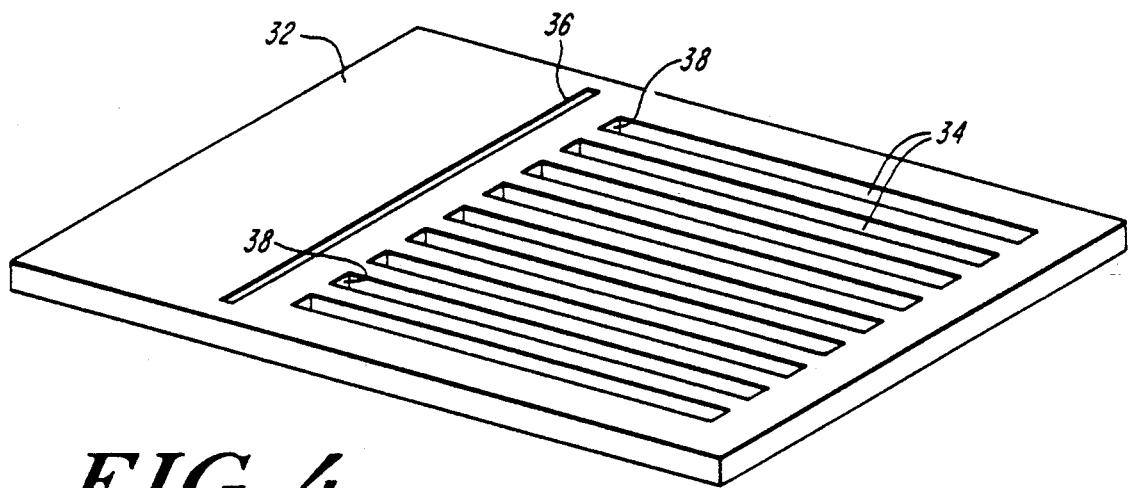
FIG. 4 shows a cast gel according to the invention prior to the addition of acceptor and ligand.

The cast gel 32 is shown in FIG. 4. The gel includes nine longitudinally oriented troughs 341 into which a second gel containing a dispersion of acceptors may be cast. The cast gel 32 also includes a horizontal trough 36 oriented perpendicular to the longitudinal troughs 34 and spaced from the parallel leading edges 38 of the longitudinal troughs 34. The thin horizontal trough 36 will receive a preparation containing ligands. The ligands may be cast into the horizontal trough 36 or placed in solution into the horizontal trough 36. The troughs 34, 36 were about 0.112" deep. As will be described in detail below, the configuration of troughs of the preferred gel is particularly suitable for measuring an affinity constant.

Acceptor-containing agarose then is prepared in the same manner as the framing gel, but at twice the concentration of agarose and detergent. After boiling to dissolve the agarose, the temperature of the agarose is lowered to between about 37 and 39 degree centigrade. Various concentrations of acceptors are prepared at twice the desired casting concentration (in electrophoresis buffer), warmed to between about 37 and 39 degrees centigrade, and mixed with an equal volume of the warm agarose. The various mixtures then are pipetted into the appropriate longitudinal trough 34. The quantity pipetted into each longitudinal trough 34 should be sufficient to fill the trough completely without overflowing. In the preferred embodiment, this quantity was about 0.6 ml. Once all of the longitudinal troughs 34 have been filled, the mixtures are allowed to fully cool and solidify. Once solidified, the tape 24 sealing opposing sides of the casting tray 18 is removed, and the formed gel, firmly attached to the GelBond TM support, is slid out of the casting tray for insertion into an electrophoresis box.

The electrophoresis box used was a "midi" sub. gel box commercially available under model H3, from Bethesda Research Laboratories, a division of Life Technologies, Inc., Gaithersburg, Md. Many commercially available electrophoresis boxes for running submerged, horizontal gels are suitable, provided that they have appropriate ports so that the electrophoresis buffer can be recirculated to prevent a build up of ions at either the anode or cathode side of the box. It also is desirable to control the temperature of the gel during electrophoresis. In the examples herein, boxes were selected to be of a convenient size for resting them on top of a bucket filled with ice.

In the preferred embodiment the power supply for the electrophoresis box may be any electrophoresis (DC) power supply capable of delivering between about 15 and 30 watts and voltages of between about 50 and 100. In the examples herein, a power supply having nominal limits of 500 volts and 200 mAmp obtained from Hoeffer Scientific, San Francisco, Cal. was used.

Electrophoresis buffer was introduced into the electrophoresis box. The electrophoresis box then was readied by placing it on an ice-filled container and levelling it In the examples herein, a styrofoam container was cut so that the electrophoresis box could be suspended by the cut edges with the bottom of the electrophoresis box in close contact with crushed ice. Tubing was connected to buffer recirculation ports so that buffer could be recirculated with the aid of a peristaltic pump from the cathode side to the anode side of the electrophoresis box. The gel containing the cast lanes of acceptors then was placed onto the central platform of the electrophoresis box and submerged in electrophoresis buffer, the box containing enough buffer so that there was at least 2 mm of buffer above the top surface of the gel. The gel was oriented within the electrophoresis box so that the longitudinal troughs 34 containing the cast lanes of acceptors are parallel to the direction of ion migration during electrophoresis.

A solution containing ligand then was carefully introduced into the submerged horizontal trough 36 using a micropipette. Between about 0.12 and 0.18 ml of ligand solution was applied. Although ligands may be gelled into the horizontal trough 36, the thinness of the well (approximately 1 mm) makes it convenient simply to apply the ligands in solution directly into the horizontal trough 36 of the cast gel 32 submerged within a buffer in an electrophoresis box, provided that the solution containing the ligand is more dense than the electrophoresis buffer. The solution containing the ligands then will sink into the horizontal trough 36 when thus applied. In the examples herein, sucrose was added to the ligand solution, to a final concentration of 6% (w/v), although it will be recognized by one of ordinary skill in the art that many other substances (e.g. glycerol, ficoll, urea etc.) could be used as well. A tracking dye (bromphenol blue, final concentration of 0.4 mg/ml) also was added to the ligand solution to aid in visualizing the sample as it was applied to the horizontal trough 34 as well as to monitor the progress of the ligands as they advance through the gel during electrophoresis. The balance of the ligand solution diluent was electrophoresis buffer containing detergent.

The gel then was electrophoresed. Leads were connected with appropriate polarities so that ligand and acceptor molecules would come into contact with each other as a result of the applied electrical field. Referring to FIG. 4, placement of the pole toward which ligand is attracted on the left side constitutes "standard orientation" and the opposite polarity constitutes "inverted orientation". In the gels of the examples contained herein, standard orientation was used, and the pole toward which the ligand was attracted was the positive pole, or anode. Power was then turned on and electrophoresis was allowed to proceed. In principle, the amount of voltage that can be used is limited primarily by heating. The precaution of cooling (as well as recirculation of buffer) permitted the use of voltages in the range of 50–80 volts that produced up to about 25 watts of heating without raising the temperature of the electrophoresis buffer much above ambient room temperature. Such voltages permitted gels containing glycosaminoglycans or proteoglycans as the ligand to be run in under two hours. A run is judged complete when the ligand has migrated sufficiently far through the longitudinal acceptor-containing lanes to resolve a difference between the mobility of ligand passing through acceptor-free lanes and lanes containing acceptor. Because the ligand molecules are not themselves visible, their migration may be estimated from the migration of the tracking dye. For example, when using buffer "(b)" heparin (a glycosaminoglycan) migrates roughly twice as far as the tracking dye bromphenol blue, while proteoglycans of various types exhibit migration rates intermediate between bromphenol blue and heparin. If the acceptors gelled into the longitudinal lanes are expected to migrate significantly in any direction during the course of the run (a test can determine this), then in judging whether the run has progressed far enough, the migration of the tracking dye should be compared not with the lanes per se, but rather with the expected new positions of the acceptors. Once the run was complete (approximately 2 hours), the power was turned off and the gel was removed from the electrophoresis box.

If the gel is being used preparatively, it may be cut into various pieces, and samples may be retrieved from the agarose by melting, electroelution, or any other convenient method as is well known to those of ordinary skill in the art.

If the gel is being used analytically, it may be convenient to fix and/or dry the gel. In some cases, the process of fixation and drying will not harm the acceptors and ligands, and the gel then may be fixed, dried, analyzed, and cut into pieces, with the samples still retrievable from the dried pieces (e.g. glycosaminoglycans can be boiled directly out of the gel) Various methods of fixation are well known to those of ordinary skill in the art. For glycosaminoglycans, it has been found that submerging the gel in 70% ethanol, with shaking, for about 30 minutes works well. For proteins, submerging the gel in 45% methanol, 5% glacial acetic acid, in water for about 30 minutes works well. If the gel is to be dried right away, fixation may not be necessary since many molecules will diffuse little during drying. Nevertheless, the exchange of buffer within the gel for alcoholic solutions offers the advantage of making gel drying more rapid. A gel may be dried by placing it for several hours in an oven at about 50° C. under vacuum Any number of standard techniques for localizing specific molecules in the gels can theoretically be used. When ligands are present at very low levels, sensitive detection methods are convenient (e.g. radioactive labelling prior to electrophoresis). Then, standard methods for gel autoradiography may be used to locate the label. For glycosaminoglycans, the radioiodination technique of Smith and Knauer (1987) Anal. Biochem 160, 104-114) worked well. Glycosaminoglycans also may be metabolically labeled with $^{35}S$-sulfate. Preferred methods of labelling protein include radioiodination and preferred methods of labelling nucleic acids include $^{32}P$ by standard methods. Nonisotopic methods also may be used (e.g. blotting, biotin, etc.).

Although the process of affinity electrophoresis may be considered a general technique for the characterization, selection, separation and/or isolation of molecules, the foregoing methods are particularly suited for situations in which the molecular interactions being measured involve the binding of a macromolecule of high electrophorectic mobility (at the operating pH of the system) to a macromolecule of low, zero, or opposite electrophoretic mobility. Some common examples include protein-DNA interactions, protein-RNA interactions, protein-glycosaminoglycan interactions and protein-proteoglycan interactions. The foregoing methods of affinity electrophoresis also are particularly suited for separations in which other conventional methods are undesirable, for example when the affinities are low, when off-rates are fast, when the amounts of the sample are limited or when coupling of molecules to a solid phase is undesirable.

According to the foregoing procedure, both the ligand and acceptor are free to migrate. It will be understood by one of ordinary skill in the art, however, that in certain circumstances it may be desirable to have one of the acceptor and ligand linked to the electrophoretic medium.

The rectangular comb 28 used in the method described above was formed as a separate piece from the comb 10. However, the rectangular comb 28 may be attached to the comb 10 in fixed relation to the parallel teeth 12.

Figure 5:
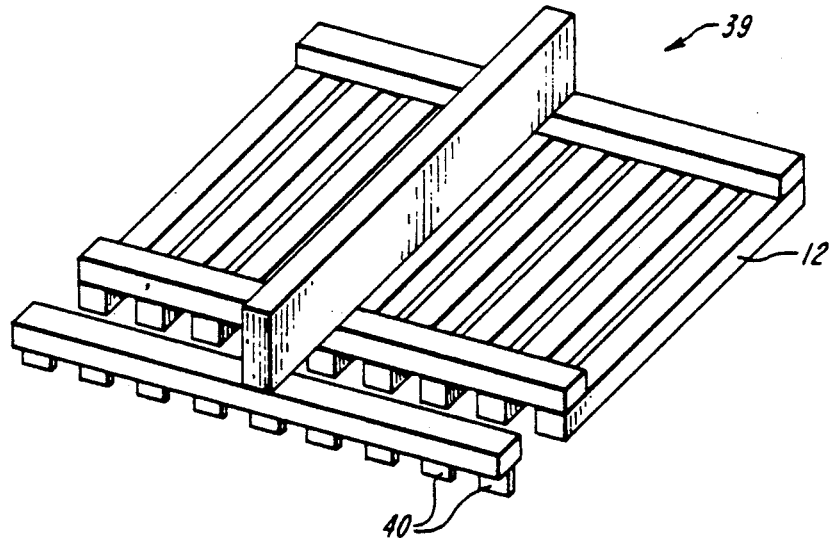
FIG. 5 is a perspective view of another embodiment of the comb of the invention.
Figure 6:
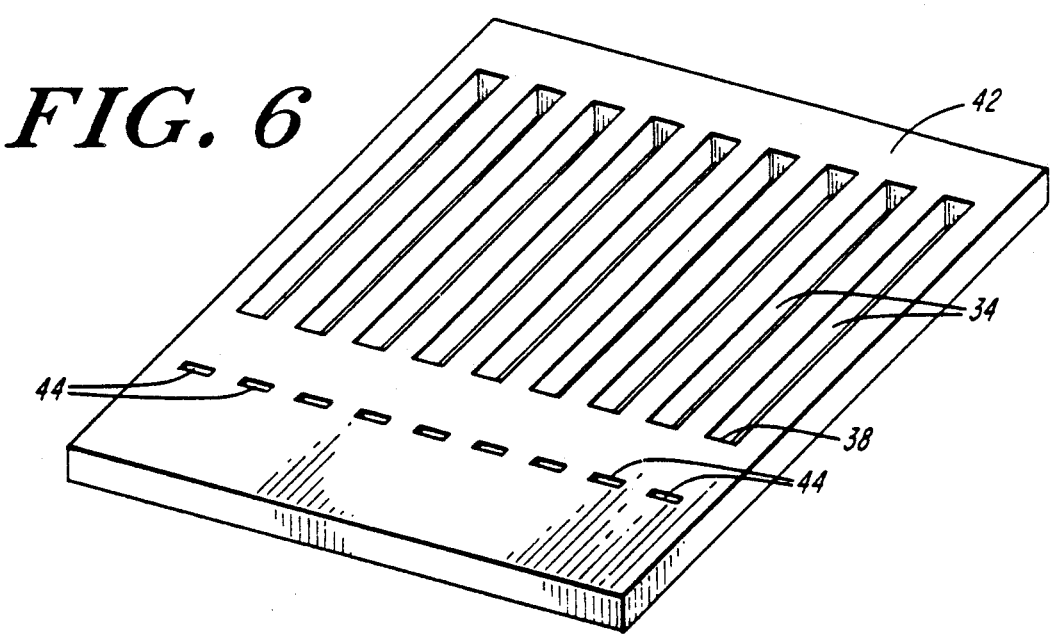
FIG. 6 is a perspective view of a cast gel formed using the comb of FIG. 5.

An alternate arrangement for a comb is shown in FIG. 5. In this embodiment, the comb 39 includes a second set of teeth 40 attached to but spaced from the first set of teeth 12. Each of the second set of teeth 40 is aligned parallel to one each of the first set of teeth. When using the comb 39 of FIG. 5, a gel may be cast as shown in FIG. 6. Like the cast gel of FIG. 4, the cast gel 42 of FIG. 6 has longitudinal troughs 34 spaced from one another and aligned parallel to their lengths. Instead, however, of a single horizontal trough spaced from and spanning the width of the combined leading edges 38 of the longitudinal troughs 34, discrete ligand troughs 44 are formed, each one of the ligand troughs 44 aligned with the longitudinal axis of a single longitudinal trough 34. When using the gel of FIG. 6, ligands are aligned only with the lanes formed by the longitudinal troughs 34, not with the acceptor-free lanes formed by the spaces between the longitudinal troughs 34. However, it should be understood that virtually any arrangement is possible, such as for example three horizontal teeth in the second set of teeth, each horizontal tooth spanning the width and aligned with three of the first set of teeth.

Figure 7:
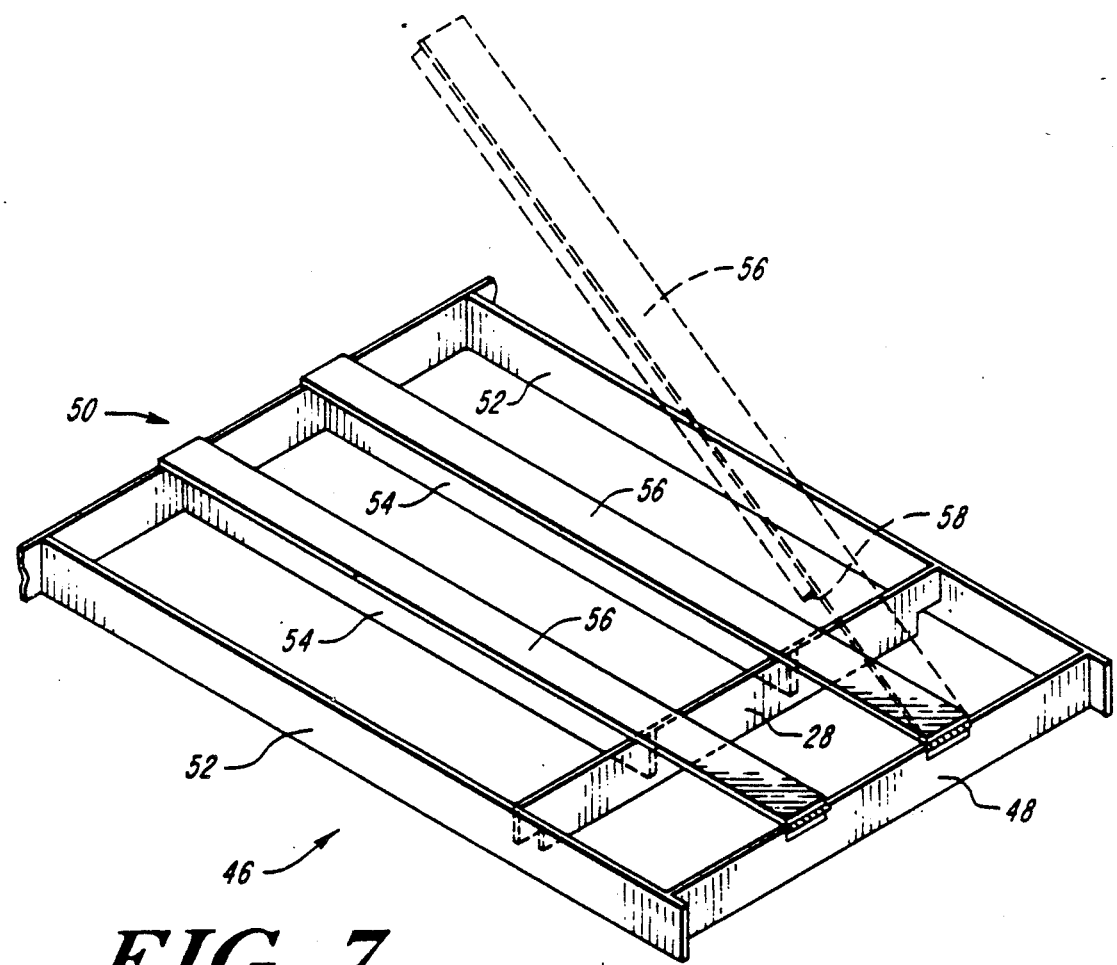
FIG. 7 is a perspective view of a casting tray of the invention.

An embodiment of a casting tray according to the invention is depicted in FIG. 7. The tray 46 is essentially a rectangular container having a detachable front wall 48, two sidewalls 52, and a bottom wall 54. The tray also includes a plurality of rectangular partitioning walls 56 defining a plurality of longitudinally aligned and parallel channels within the tray 46. These partitioning walls 56 preferably are movable with respect to the tray 46, and most preferably are pivotally attached to the front wall 48 by, for example, a hinge. As shown by the phantom image, the partition walls 56 then may be pivoted upwardly and out of the gel-forming area defined by the tray 46.

Preferably, the partitioning walls 56 have a length shorter than the distance between the rear end 50 and the front wall 48 of the tray 46, the length of the partitioning walls 56 being equal such that their free edges 58 are parallel to one another. A rectangular comb 28 then may be positioned sealingly against the free edges 58 of the partitioning walls 56, the rectangular comb 28 being securable to slots within and spanning the distance between the sidewalls 52 of the tray 46.

The partitioning walls 56 may be as wide as the teeth of the comb 10 described in connection with FIGS. 1 and 5. The partitioning walls may be attached to one another (not shown) and pivotable only as a unit or may be pivotable independent of one another. The spaces between the partitioning walls 56 then may be filled with a gel and the partitioning walls 56 may be pivoted out of contact with the gel once it solidifies to form troughs. Alternatively, the spaces between the partitioning walls may be filled with different concentrations of acceptor-containing gel, then once the acceptor-containing gel solidifies, the partitioning walls 56 may be pivoted out of contact with the solidified gel and the troughs formed by the partitioning walls 56 may be filled with a gelling material that does not contain any acceptor molecules. The rectangular comb 28 may be removed to form the ligand receiving trough.

If the partitioning walls are independently movable, then the size of the lanes into which the acceptor-containing gel is introduced may easily be varied by moving selected partitioning walls out of the gel forming area prior to introducing the gel.

If the rectangular comb 28 abuts and sealingly mates with the free edges 58 of the partitioning walls, then it will be understood that the mating surfaces must be constructed and arranged to seal with one another to prevent leakage between the lanes if the lanes are being filled with different concentrations of acceptor-containing molecules. It is not necessary, however, in all embodiments for the rectangular comb to sealingly abut the free edges 58 of the partitioning walls 56. Instead, comb arrangements such as those shown in FIGS. 2 and 5 may be movably attached to a casting tray in order to insure quick and proper alignment of the comb with respect to the casting tray.

Figure 8:
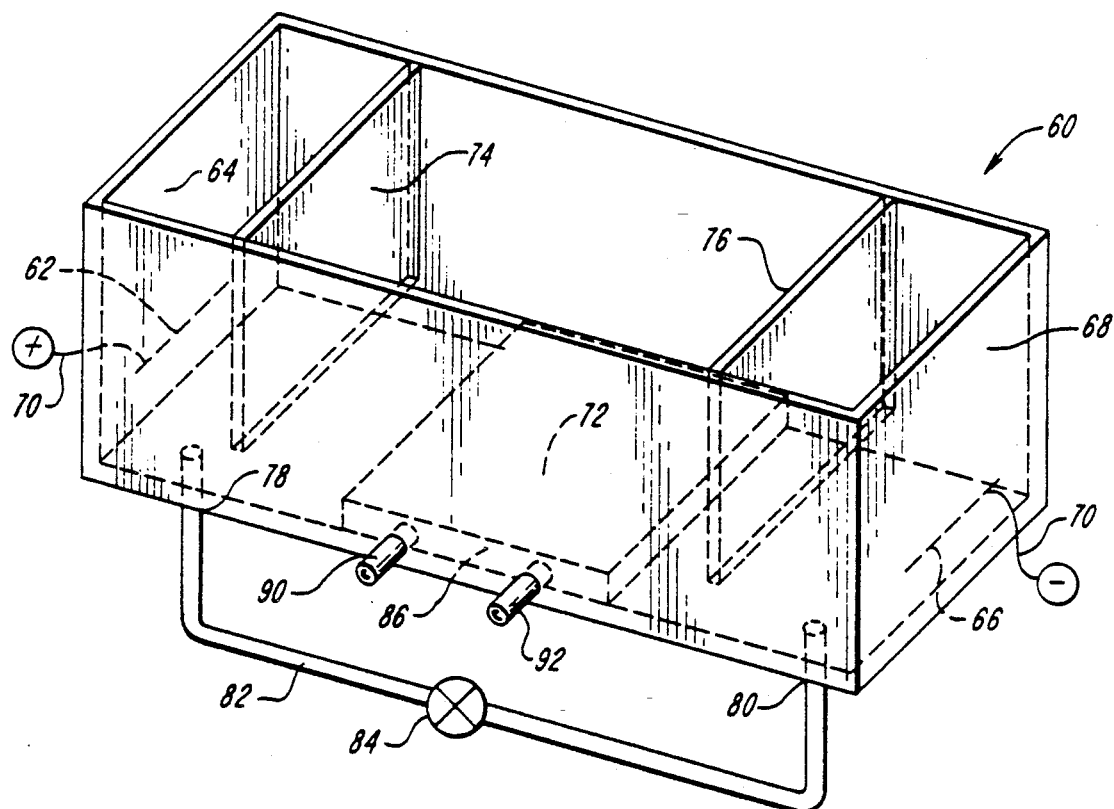
FIG. 8 is a perspective view of the electrophoresis apparatus of the invention.

A preferred electrophoresis box for use in accordance with the invention is shown in FIG. 8. The electrophoresis box includes a container 60 for containing a volume of buffer. The container preferably is rectangular, having four sidewalls and a bottom wall As in conventional electrophoresis boxes, an anode 62 is located adjacent to first sidewall 64 and defines an anode side of the container. A cathode 66 is located adjacent to a second sidewall 68 opposite the first sidewall 64, and defines a cathode side of the container. Electrical leads 70 are attached to the anode 62 and cathode 66 for generating an electric potential between the anode 62 and cathode 66. Centrally between the anode 62 and cathode 66 is a platform 72 for supporting a gel. A conventional box partition wall 74 is located between the anode 62 and the side of the platform closest to the anode. This box partition wall 74 extends from side to side parallel to the first sidewall 64 but does not extend completely to the bottom wall of the container, thereby allowing fluid communication from the platform side of the box partition wall 74 to the anode side of the box partition wall 74. A second box partition wall 76 also is positioned between cathode 66 and the cathode end of the platform 72 closest to the cathode 66

Figure 9:
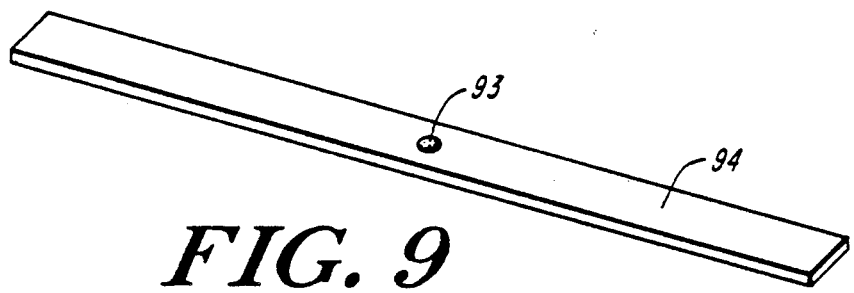
FIG. 9 is a perspective view of a gel containing a heterogeneous mix of ligands.
Figure 10:
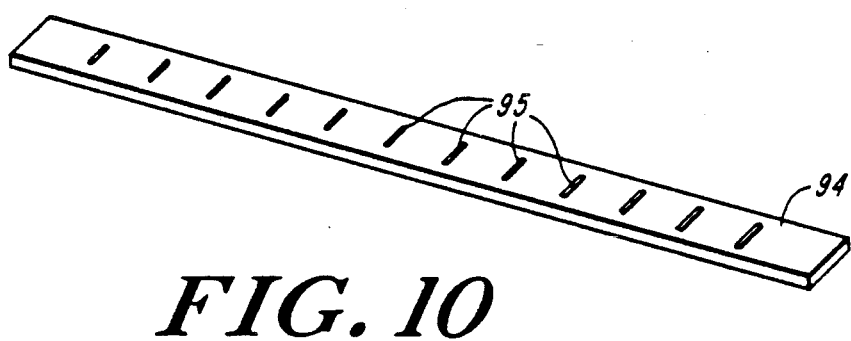
FIG. 10 is a perspective view of the gel of FIG. 9 after applying an electrophoretic charge.
Figure 11:
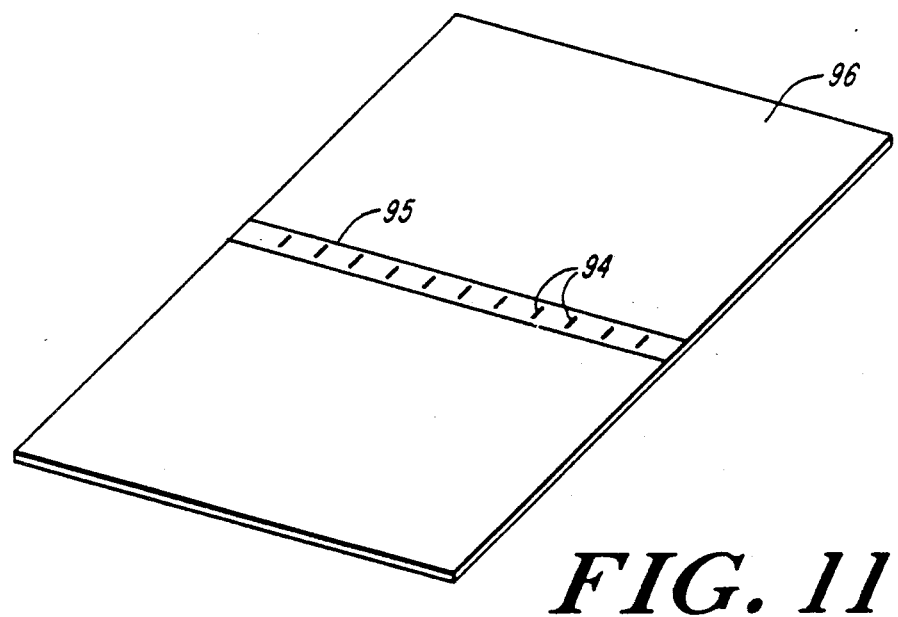
FIG. 11 is a perspective view of the gel of FIG. 10 cast into a larger gel.
Figure 12:
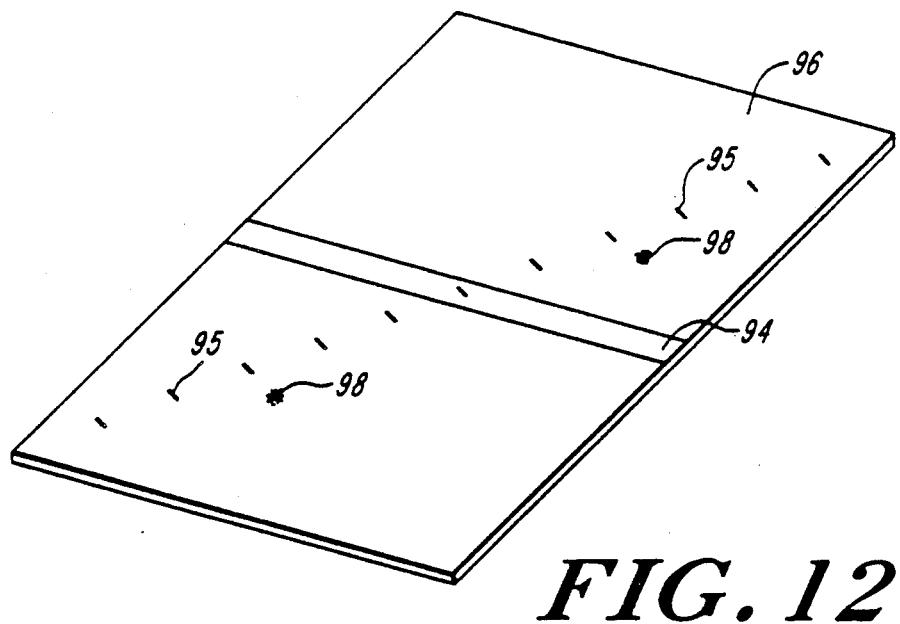
FIG. 12 is a perspective view of the gel of FIG. 11 after applying an electrophoretic charge.

Unlike conventional electrophoresis boxes, the electrophoresis box of the invention includes both a buffer recirculation loop for preventing the build up of ions at the anode or cathode and a cooling chamber for controlling the temperature of the electrophoresis buffer. An anode port 78 is in fluid communication with the anode side of the container between the first box partition wall 74 and the first sidewall 64. A cathode port 80 is in fluid communication with the cathode side of the container between the second box partition wall 76 and second sidewall 68. A conduit such as a tube 82 may connect these ports and allow recirculation of ions building up on one side of the container to the other side of the container. Recirculation may be assisted, for example, by a peristaltic pump 84. The electrophoresis box of the invention also includes a coolant chamber 86 which is formed in part by the interior bottom wall of the container. This chamber 86 has a fluid inlet port 90 and a fluid outlet port 92, such that a coolant (e.g. cool tap water) may be circulated through the chamber to cool the electrophoresis buffer and to control the temperature during electrophoresis When screening a heterogeneous mix containing molecules having different electrophoretic mobilities due to being differently charged, a preferred procedure is followed. The mix 93 first is applied to the center of a nonrestrictive gel cast as a strip 94 (FIG. 9). Then, the mix 93 is electrophoresed for a sufficient period of time to cause the mix to separate into subfractions 95 based upon relative electrophoretic mobility (FIG. 10). Next, the entire strip of FIG. 10 is cast into a larger gel 96 containing acceptor (FIG. 11). Electrophoretic conditions then are applied to the larger gel, the charge being oriented across the gel at 90 degrees to the orientation of the charge previously applied to the strip 94. The molecules in the strip having no affinity for acceptor will migrate unhindered by the acceptor at a rate relative to their position in the strip, the molecules at either end of the strip migrating fastest but in opposite direction. At any time during electrophoresis, the position of the subpopulations having no affinity for acceptor should be oriented generally in a line at an angle to the strip (FIG. 12). Any molecules, however, having an affinity for acceptor and slowed by interaction with the acceptor should be displaced from this line. Thus, those molecules with an affinity for acceptor may be identified by their position remote from this line. In FIG. 12, the molecules having an affinity for the acceptor are indicated by the spots numbered 98.

It should be understood that alternatively the subfractions in the strip also may be isolated from one another and electrophoresed separately. In this case, the molecules in the subfraction isolated will have the same electrophoretic mobility, and therefore may be electrophoresed through a single concentration of acceptor or through multiple lanes containing differing concentrations of acceptor.

As discussed above, the foregoing methods may be used for determining the affinity constant of two molecules. At equilibrium, the affinity constant is defined as follows:

$$K = \frac{[A][L]}{[AL]}$$

wherein K is the equilibrium dissociation constant; [L] represents the concentration of unbound ligand molecule; [A] represents the concentration of unbound acceptor molecule; and [AL] represents the concentration of acceptor-ligand complex.

Since $[A]_t = [A] + [AL]$, wherein $[A]_t$ represents the total concentration of A (bound plus free), $[A]_t - [AL]$ may be substituted for [A] as follows:

$$K = \frac{([A]_t - [AL])[L]}{[AL]}$$

$$K = \frac{[A]_t[L]}{[AL]} - [L]$$

When $[L] << K$, then the free [L] term may be deleted from the right hand side of the equation, so that $$K = \frac{[A]_t[L]}{[AL]}$$

Since $[L]_t = [L] + [AL]$, wherein $[L]_t$ represents the total concentration of L (bound plus free), $[L]_t - [AL]$ may be substituted for [L] as follows:

$$K = \frac{[A]_t([L]_t - [AL])}{[AL]}$$

$$K = \frac{[A]_t[L]_t}{[AL]} - [A]_t$$

or $$K + [A]_t = \frac{[A]_t[L]_t}{[AL]}$$

Dividing both sides by $[A]_t$, the $$K \frac{(1)}{([A]_t)} + 1 = \frac{[L]_t}{[AL]} \quad \text{(Equation 1)}$$

Thus, Equation 1 relates the concentration of the complex AL to the concentration of A and L initially put into the system, assuming that [L] is negligible as compared to K.

According to the invention, the ligand molecule is introduced at a concentration $[L]_t$ into the horizontal well. Since $[L]_t$ is always greater than [L], the condition that [L] is negligible as compared to K will always be true whenever $[L]_t << K$. If the value of $[L]_t$ is known, then it can be determined whether this condition holds if the expected lower limit for K is known. Alternatively, affinity electrophrosis may be performed to measure K, and then determine post-hoc whether the $[L]_t$ was indeed $<< K$. If not, affinity electrophoresis may be performed using less L. Even if both the value of $[L]_t$ and the expected value of K are unknown, affinity electrophoresis may be performed at different dilutions of L. When $[L]_t << K$, the results of the affinity electrophoresis using different dilutions should give the same calculated value for K, no matter what the value of $[L]_t$.

The inverse of the above equation is:

$$\frac{[AL]}{[L]_t} = \frac{1}{1 + K/[A]_t} \quad \text{(Equation 2)}$$

Since $[AL]/[L]_t$ is by definition equal to the fraction of L bound when [L] meets [A], then the fraction of L bound at equilibrium may be defined by the right hand side of the above equation when L and AL are in equilibrium. It is safe to assume that L and AL are in equilibrium when binding and dissociation between A and L are very fast compared to the duration of the electrophoresis. In other words, equilibrium will exist for acceptors and ligands having fast on- and off-rates compared to the duration of the electrophoresis.

The relative concentration of L and A also will influence the dynamics of the interaction of L and A. If L molecules migrate through a zone in which $[A]_t >> K$, then the L-front will behave as though L-molecules are bound all the time. In other words, the L-front will have the same mobility as the complex AL. If L-molecules migrate through a zone containing $[A]_t << K$, then the L-front will behave as though no L-molecules are bound, and the L-front will have the mobility of the L-molecules. If, however, the L-molecules migrate through a zone containing $[A]_t = K$, then by equation 2, the fraction of L bound would equal one-half and the L-front should exhibit a mobility half-way between that of L and AL. This relationship between mobility and $[A]_t$ can be stated in a more general and comprehensive way:

Defining $M_0$ as the mobility of L, $M_c$ as the mobility of the complex AL, and M as the mobility of the L-front when migrating through a zone containing acceptor molecules at a concentration = $[A]_t$, then it follows that the fraction of L molecules bound when $[A]_t = X$ is related to the mobility of the L-front when $[A]_t = X$ by the relation:

$$\text{fraction bound} = \frac{M - M_o}{M_c - M_o}$$

Consequently, from equation 2, $$\frac{M_c - M_o}{M - M_o} = 1 + \frac{K}{[A]_t}$$

Rearranging, $$\frac{1}{M - M_o} = \frac{1}{M_c - M_o} + \frac{K}{[A]_t(M_c - M_o)}$$

This equation then relates the mobility of the L-front to the concentration $[A]_t$ in each lane, according to the formula for a straight line.

$$Y = "m"x + b$$

wherein the slope "m" = $K/M_c - M_o$
and the Y intercept = $1/M_c - M_o$
provided $1/[A]_t$ is plotted on the X-axis and $1/M - M_o$ is plotted on the Y-axis.

K therefore may be calculated by producing such a plot and dividing its slope by its y-intercept.

EXAMPLE 1

Affinity co-electrophoresis was run according to general procedure described above using a heterogeneous sample of heparin as the ligand molecules and using antithrombin III as the acceptor molecule. Porcine heparin was obtained from SIGMA Chemical Corp., St. Louis, Mo., radiodinated according to the procedure of Smith and Knauer and was at a known concentration of 7.5 ng/ml, and a specific activity of $1.4 \times 10^8$ dpm of $^{125}I$ per microgram of heparin. The heparin was radioactively labeled so that its migration could be tracked. Human Antithrombin III was a gift of Dr. R. Rosenberg, MIT, and was dispersed across nine lanes at concentrations ranging from 1,000 nM to 1 nM. The results, an autoradiogram of the gel after fixing in 70% alcohol and drying, are shown in FIG. 13 and demonstrate that the sample of heparin contained at least two populations of heparin, one population designated 100, having an affinity for antithrombin III, and another 102 having essentially no detectable affinity for antithrombin III. As can be seen, the population 100, having an affinity for antithrombin III, was slowed during migration by contact with the antithrombin III, whereas the population having no affinity for antithrombin III moved along with the front and was not slowed by contact with antithrombin III. The front is indicated by heparin migrating through antithrombin III-free lanes of gel formed between the lanes containing antithrombin III. These acceptor-free lanes act as controls and establish the migration of the front relative to migration through a field of acceptors.

EXAMPLE 2

The subfractions of heparin separated in Example 1 and located by the autoradiogram of FIG. 13 were eluted from the dried gel. This was accomplished by immersing pieces of the dried gel in a very small volume of electrophoresis buffer and boiling. The subfractions were designated as an antithrombin III "non-binding" fraction and an antithrombin III "binding" fraction. These fractions again were run in affinity co-electrophoresis, each fraction being electrophoresed through three lanes containing different concentrations of antithrombin III ranging from 1,500 nM to 100 nM. The gel was cast to have three ligand troughs, each ligand trough aligned with and spanning the width of three lanes containing acceptor at different concentrations. As shown in FIG. 14, the "non binding" fraction electrophoresed through the lanes containing antithrombin III and was not slowed relative to the front. However, the "binding" subfraction was slowed during its migration through the lanes containing antithrombin III, thereby demonstrating that two distinct subpopulations were in fact isolated.

EXAMPLE 3

Affinity co-electrophoresis was run according to the general procedure described above using low molecular weight heparin, radioiodinated, as the ligand and using basic FGF as the acceptor The low molecular weight heparin (obtained by Sephadex G100 gel filtration chromatography of total heparin and pooling of the 5% of the heparin that was last to elute) was at a known concentration of 4 ng/ml and a specific activity of $1.4 \times 10^8$ dpm of $^{125}I$ per microgram of heparin. The basic FGF (purified from bovine brain according to procedures of Lobb & Fett (1984) Biochemistry 23, pp. 6295-6299 was dispersed throughout nine lanes at concentrations ranging from 40 nM to 0.01 nM. The length of the basic FGF containing lanes was about 1.8". The nine lanes were separated from one another by acceptor-free lanes. The results of the co-electrophoresis are shown in FIG. 15.

EXAMPLE 4

The equilibrium affinity constant of low molecular weight heparin with respect to basic FGF then was determined. The migration front of the labelled heparin (designated 104 in FIG. 15) represents heparin passing through acceptor-free lanes of gel formed between the lanes of gel containing acceptor. The thick bands 106 represent heparin that has been slowed by contact with the acceptor molecules. The mobility shift ($M-M_o$) was determined as the distance between the front and the slowed bands. Then, according to the formulas described above, K was determined by plotting the inverse of the mobility shift on the Y axis and the inverse of the concentration of the basic FGF on the X axis. The affinity constant was determined to be 2.2 nM. This was consistent with previously reported values determined by conventional procedures.

It should be understood that the foregoing description of the invention is intended merely to be illustrative thereof and that other embodiments modifications and equivalents will be apparent to those of ordinary skill in the art without departing from the spirit and scope of the invention.

What I claim is:

1. A comb adapted for use in preparing a gel for use in electrophoresis, the comb comprising:
   first teeth attached in fixed relation to one another, each tooth having a length defining a longitudinal axis, a width and a height, the length being substantially greater than the width and the longitudinal axis being substantially parallel;
   means attached to the teeth for providing a gripping handle; and
   a perpendicular tooth attached to the first teeth, the perpendicular tooth having a length spanning the combined width of at least two of the first teeth and being oriented perpendicularly to and intersecting the longitudinal axes.

2. A comb as claimed in claim 1 wherein each tooth defines a substantially flat rectangular bottom surface, the bottom surfaces lying int he same plane, and wherein the teeth are attached to one another remote from their bottom surfaces.

3. A comb as claimed in claim 2 wherein the perpendicular tooth is spaced along the longitudinal axes from the first teeth.

4. A comb as claimed in claim 1, wherein the perpendicular tooth is spaced along the longitudinal axes from the first teeth.

5. A comb adapted for sue in preparing a gel for electrophoresis, the comb constructed and arranged to form simultaneously within a gel a plurality of aligned, parallel lanes each having a length substantially greater than its width and defining a longitudinal axis, the lanes being parallel along their lengths, and single lane oriented perpendicularly to the longitudinal axis of each of the parallel lanes, the single lane spanning the combined width of at least two of the parallel lanes and intersecting the longitudinal axis of at least two of the parallel lanes.

6. A comb as claimed in claim 5, wherein the comb is constructed and arranged such that the single lane is formed at a location spaced from each of the parallel lanes along the longitudinal axis of each of the parallel lanes.

7. A comb adapted for use in preparing a gel for use in electrophoresis, the comb comprising:
   first teeth attached in fixed relation to one another, each tooth having a length defining a longitudinal axis, a width and a height, the length being substantially greater than the width and the longitudinal axes being substantially parallel;
   means attached to the teeth for providing a gripping handle; and
   a perpendicular tooth attached to and spaced from the first teeth, along the longitudinal axes.

* * * * *